United States Patent
Lange et al.

(10) Patent No.: US 10,517,812 B2
(45) Date of Patent: Dec. 31, 2019

(54) PRODUCT AND METHOD FOR THE TEMPORARY SHAPING OF KERATIN-CONTAINING FIBERS

(71) Applicant: HENKEL AG & CO. KGAA, Düsseldorf (DE)

(72) Inventors: Julia Bibiane Lange, Sievershütten (DE); Anna Puls, Winsen (DE); Cyrielle Martinez, Hamburg (DE); Bernd Richters, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 29 days.

(21) Appl. No.: 15/556,622

(22) PCT Filed: Jan. 26, 2016

(86) PCT No.: PCT/EP2016/051566
§ 371 (c)(1),
(2) Date: Sep. 8, 2017

(87) PCT Pub. No.: WO2016/142092
PCT Pub. Date: Sep. 15, 2016

(65) Prior Publication Data
US 2018/0055757 A1   Mar. 1, 2018

(30) Foreign Application Priority Data
Mar. 9, 2015  (DE) .......................... 10 2015 204 152

(51) Int. Cl.
*A61K 8/81*  (2006.01)
*A61Q 5/06*  (2006.01)
*A61K 8/41*  (2006.01)

(52) U.S. Cl.
CPC ............. *A61K 8/8152* (2013.01); *A61K 8/41* (2013.01); *A61K 8/8147* (2013.01); *A61K 8/8176* (2013.01); *A61K 8/8182* (2013.01); *A61Q 5/06* (2013.01); *A61K 2800/594* (2013.01)

(58) Field of Classification Search
CPC .. A61K 2800/594; A61K 8/41; A61K 8/8147; A61K 8/8152; A61K 8/8176; A61K 8/8182; A61Q 5/06
See application file for complete search history.

(56) References Cited

U.S. PATENT DOCUMENTS

| 2014/0093467 A1* | 4/2014 | Knappe ................ A61K 8/8152 424/70.15 |
| 2018/0042834 A1* | 2/2018 | Lange ........................ A61Q 5/06 |
| 2018/0055756 A1* | 3/2018 | Lange ........................ A61Q 5/06 |
| 2018/0055758 A1* | 3/2018 | Lange ........................ A61Q 5/06 |

FOREIGN PATENT DOCUMENTS

| DE | 102011077364 | * | 12/2012 | |
| WO | 2011057882 A1 | | 5/2011 | |
| WO | WO 2011/057882 | * | 5/2011 | ............... A61K 8/04 |
| WO | 2012072774 A1 | | 6/2012 | |
| WO | WO 2013/072118 | * | 5/2013 | |
| WO | 2014095163 A2 | | 6/2014 | |

OTHER PUBLICATIONS

Tilamar Fix A140 (Multi-functional Styling Polymer, DSM pp. 1-44). (Year: 2015).*
Personal Care, Strong Hold Without Stickiness https://www.personalcaremagazine.com/story/9759/features, May 1, 2012). (Year: 2012).*
EPO, International Search Report and Written Opinion issued in International Application No. PCT/EP2016/051566, dated Mar. 16, 2016.
Ashland, "Ashland Brings Performance and Style to Crystal Clear Gel with AquaStyle: New, Higlhy Functional Polymer for Hair Styling Formulations Offers Consumer-Perceivable Styling Benefits That Stand up to High Humidity Conditions", Apr. 1, 2014.

* cited by examiner

*Primary Examiner* — Anna R Falkowitz
(74) *Attorney, Agent, or Firm* — Lorenz & Kopf, LLP

(57) ABSTRACT

The disclosure relates to a cosmetic composition for the temporary shaping of hair, containing a combination of two specific anionic acrylate copolymers. The cosmetic composition provides an extremely good moisture resistance.

9 Claims, No Drawings

PRODUCT AND METHOD FOR THE TEMPORARY SHAPING OF KERATIN-CONTAINING FIBERS

CROSS-REFERENCE TO RELATED APPLICATION

This application is a U.S. National-Stage entry under 35 U.S.C. § 371 based on International Application No. PCT/EP2016/051566, filed Jan. 26, 2016 which was published under PCT Article 21(2) and which claims priority to German Application No. 10 2015 204 152.2, filed Mar. 9, 2015, which are all hereby incorporated in their entirety by reference.

TECHNICAL FIELD

The present disclosure relates to a cosmetic composition for fixing hair or for the temporary reshaping of keratin fibres, in particular human hair, wherein the composition contains a combination of two anionic acrylate polymers.

BACKGROUND

The temporary styling of hairstyles for a longer period up to a number of days generally requires the application of active fixing agents. Hair treatment products which serve to temporarily shape the hair therefore play a key role. Suitable products for temporary shaping usually contain synthetic polymers and/or waxes as active fixing agent. Products for assisting the temporary reshaping of keratin-containing fibres can be formulated for example as a hairspray, hair wax, hair gel or hair mousse.

The most important property of a product for temporarily shaping hair, also referred to hereinafter as styling agents, lies in providing the treated fibres in the newly modelled form—i.e. a form impressed onto the hair—with the strongest hold possible. Reference is also made to a strong hairstyle hold or a high degree of hold of the styling agent. The hairstyle hold is determined substantially by the type and amount of the active fixing agents used, wherein the further constituents of the styling agent however can also make a contribution.

Besides a high degree of hold, styling agents must meet a wide range of further requirements. These can be divided roughly into properties on the hair, properties of the particular formulation, for example properties of the mousse, the gel, or the sprayed aerosol, and properties which concern the handling of the styling agent, wherein the properties on the hair are attributed particular importance. The following should be mentioned in particular: moisture resistance, low tack, and a balanced conditioning effect. Furthermore, a styling agent should be universally usable for all hair types where possible and should be mild on the hair and skin.

In order to meet the different requirements, a large number of synthetic polymers have already been developed as active fixing agents and are used in styling agents. The polymers can be divided into cationic, anionic, non-ionic and amphoteric fixing polymers. When applied to the hair, the polymers ideally provide a polymer film which on the one hand provides the hairstyle with a strong hold, but on the other hand is sufficiently flexible so as not to break under stress. If the polymer film is too fragile, what are known as film flakes form, i.e. residues, which come loose as the hair moves and give the impression that the user of the corresponding styling agent has dandruff. Similar problems occur when waxes are used as active fixing agent in the styling agent. If the styling agent is a gel or a paste, the polymers should additionally have thickening properties.

Known anionic polymers that can be used in hair fixing products are acrylate copolymers having two or more structural units. Specific terpolymers of this type obtained by emulsion polymerization of the monomers n-butyl methacrylate, methacrylic acid, and ethyl acrylate are described in the international application WO 2012/072774 A1. The international application WO 2014/095163 A1 describes the use of corresponding terpolymers in hair mousses for improving hair volume.

Hydrophobically modified acrylate copolymers (INCI: Acrylates Copolymer (and) Water) are also commercially available and act fundamentally as thickening agent. The datasheet AquaStyle® SH-100 Polymer (Ashland Inc.) describes such an acrylate copolymer and use thereof in combination with carbomers. A suitability for crystal-clear hair gels, good initial stiffness, moisture resistance and durable effect are described.

The object as contemplated herein was to provide further suitable polymer combinations which are exemplified by good film-forming and/or fixing properties, have a high degree of hold without having to compromise on flexibility or good moisture resistance—in particular resistance to perspiration and water—and additionally are suitable for the production of stable viscous and also stable transparent cosmetic compositions. In particular, currently obtainable styling agents can be improved yet further because a good combination of stiffness and long-term hold (high humidity curl retention) is not always sufficiently ensured. The object as contemplated herein is therefore to provide such styling agents which, in addition to the above-mentioned properties, provide in particular both good stiffness and good long-term hold.

BRIEF SUMMARY

A cosmetic composition for temporarily reshaping keratin fibres is provided herein. The cosmetic composition includes at least one acrylate copolymer (a). The at least one acrylate copolymer (a) is constructed at least from the following monomer units: n-butyl methacrylate, methacrylic acid, and ethyl acrylate. The cosmetic composition further includes at least one anionic acrylate copolymer (b). The at least one anionic acrylate copolymer (b) is constructed at least from the following monomer units: at least one (meth)acrylic acid unit, at least one (meth)acrylic acid ethyl ester unit, and at least one (meth)acrylic acid ester unit. The at least one (meth)acrylic acid ester unit is different from the (meth)acrylic acid ethyl ester unit (b2) and includes a hydrophobic group as ester group.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

This has been achieved as contemplated herein by a combination of two specific anionic acrylate polymers different from one another.

The following is provided by the present disclosure:
1. A cosmetic composition for temporarily reshaping keratin fibres, said composition containing:

(a) at least one acrylate copolymer (a) which is constructed at least from the following monomer units:
(a1) n-butyl methacrylate,
(a2) methacrylic acid,
(a3) ethyl acrylate,
and
(b) at least one anionic acrylate copolymer (b) which is constructed at least from the following monomer units:
(b1) at least one (meth)acrylic acid unit
(b2) at least one (meth)acrylic acid ethyl ester unit
(b3) at least one (meth)acrylic acid ester unit which is different from the (meth)acrylic acid ethyl ester unit (b2) and comprises a hydrophobic group as ester group.

2. The cosmetic composition according to point 1, wherein the at least one acrylate copolymer (a), in relation to the weight of the copolymer (a), comprises from about 60 to about 80% by weight of n-butyl methacrylate, from about 10 to about 30% by weight of n-methacrylic acid, and from about 5 to about 15% by weight of ethyl acrylate.

3. The cosmetic composition according to either one of the preceding points, wherein the copolymer (a) is produced by emulsion polymerization.

4. The cosmetic composition according to any one of the preceding points, wherein the composition contains the copolymer (a) in a proportion of from about 0.2 to about 4.0% by weight, preferably from about 1.0 to about 3.5% by weight, and in particular from about 1.5 to about 3.0% by weight, in relation to the total weight of the cosmetic composition.

5. The cosmetic composition according to any one of the preceding points, wherein the anionic acrylate copolymer comprises (b) methacrylic acid as monomer unit (b1) and ethyl acrylate as monomer unit (b2).

6. The cosmetic composition according to any one of the preceding points, wherein the anionic acrylate copolymer (b) comprises a (meth)acrylic acid alkyl ester as monomer unit (b3).

7. The cosmetic composition according to any one of the preceding points, wherein the composition contains the anionic acrylate copolymer (b) in a proportion of from about 0.1 to about 5.0% by weight, preferably from about 1.0 to about 4.0% by weight, and in particular from about 1.5 to about 3.0% by weight, in relation to the total weight of the cosmetic composition.

8. The cosmetic composition according to any one of the preceding points, wherein the anionic acrylate copolymer (b), with a solids content of 2% by weight in an aqueous neutralized solution at 25° C., has a viscosity of from about 60,000 to about 120,000 cPs.

9. The cosmetic composition according to any one of the preceding points, wherein the anionic acrylate copolymer (a) is one with the INCI name Acrylates Copolymer, in particular Tilamar® Fix (DSM).

10. The cosmetic composition according to any one of the preceding points, wherein the anionic acrylate copolymer (b) is one with the INCI name Acrylates Copolymer (and) Water, in particular AquaStyle™ SH-100 (Ashland Inc.).

11. The cosmetic composition according to any one of the preceding points, wherein the anionic acrylate copolymer (a) is one with the INCI name Acrylates Copolymer and the anionic acrylate copolymer (b) is one with the INCI name Acrylates Copolymer (and) Water.

12. The cosmetic composition according to any one of the preceding points, wherein the anionic acrylate copolymer (a) is Tilamar® Fix (DSM) and the anionic acrylate copolymer (b) is AquaStyle™ SH-100 (Ashland Inc.).

13. The composition according to any one of the preceding points, which, in relation to the total weight of the cosmetic composition, contains:
from about 0.5 to about 10% by weight of the anionic acrylate copolymer (a), and
from about 0.1 to about 15% by weight of the anionic acrylate copolymer (b).

14. The cosmetic composition according to any one of the preceding points, containing, in relation to the total weight of the cosmetic composition:
from about 4.0 to about 8.0% by weight of the anionic acrylate copolymer (a), and
from about 5.0 to about 10% by weight of the anionic acrylate copolymer (b).

15. The cosmetic composition according to any one of the preceding points, wherein the composition also contains at least one polymer (c) different from the acrylate copolymers (a) and (b), in particular an anionic or non-ionic polymer (c).

16. The cosmetic composition according to any one of the preceding points, exemplified in that, in relation to its total weight, it also contains
c) from about 1.0 to about 10% by weight of polyvinylpyrrolidone and/or vinylpyrrolidone/vinyl acetate copolymer, preferably polyvinylpyrrolidone.

17. The cosmetic composition according to point 16, exemplified in that the proportion by weight of the polyvinylpyrrolidone and/or vinylpyrrolidone/vinyl acetate copolymer c) in the total weight of the cosmetic composition is from about 2.0 to about 8.5% by weight, preferably from about 3.0 to about 7.0% by weight.

18. The cosmetic composition according to any one of the preceding claims, wherein the composition contains water in a proportion of from about 50 to about 95% by weight, preferably between about 60 and about 90% by weight, and in particular between about 65 and about 85% by weight, in relation to the total weight of the cosmetic composition.

19. The cosmetic composition according to any one of the preceding claims, wherein the composition is present in the form of a hair gel, hairspray, hair mousse or hair wax, in particular in the form of a hair gel.

20. Use of a cosmetic composition according to any one of points 1 to 19 for temporarily reshaping keratin fibres.

21. Use of a cosmetic composition according to any one of points 1 to 19 for improving the moisture resistance of temporarily shaped keratin fibres.

22. A method for the temporary shaping of keratin fibres, in particular human hair, in which the cosmetic composition according to any one of points 1 to 19 is applied to keratin fibres.

Within the scope as contemplated herein, it has been surprisingly found that by combining two constituents known per se, which are already used in styling products, an improved moisture resistance of styling products can be obtained. Other properties usually required of styling products, such as long-term hold, stiffness and low tack, are retained. A good combination of properties in this way was not expected, not even in the knowledge of the individual components, and was surprising. It was found, by way of experimentation, that the combination of the two components resulted in an effect going beyond the added effects of the individual components, i.e. a synergistic effect, in terms of the moisture resistance, which became evident in the HHRC (high humidity curl retention) test).

The term keratin fibres includes fur, wool and feathers as contemplated herein, but in particular human hair.

The essential constituents of the cosmetic composition as contemplated herein are the anionic acrylate copolymer (a)

and the anionic acrylate copolymer (b), which is different from the acrylate copolymer (a).

The copolymers (a) used as contemplated herein are obtained by polymerization, in particular by emulsion polymerization, of the monomers n-butyl methacrylate, methacrylic acid, and ethyl acrylate and optionally further monomers. By way of example, ethyl methacrylate is preferably suitable as further monomer. Preferred copolymers (a) include to an extent of at least 90% by weight, preferably at least 95% by weight, and in particular at least 97% by weight of the monomers n-butyl methacrylate, methacrylic acid and ethyl acrylate. Copolymers (a) that have been obtained as terpolymers exclusively from the monomers n-butyl methacrylate, methacrylic acid and ethyl acrylate are particularly preferred.

In a preferred embodiment the copolymers (a) comprise, in relation to their weight, from about 60 to about 80% by weight of n-butyl methacrylate, from about 10 to about 30% by weight of methacrylic acid, and from about 5 to about 15% by weight of ethyl acrylate, wherein copolymers (a) having a proportion by weight of the monomers of from about 65 to about 75% by weight of n-butyl methacrylate, from about 15 to about 25% by weight of methacrylic acid, and from about 8 to about 12% by weight of ethyl acrylate are particularly preferred. Very particularly preferred copolymers (a) have a proportion by weight of the monomers of from about 67 to about 72% by weight of n-butyl methacrylate, from about 18 to about 23% by weight of methacrylic acid, and from about 9 to about 11% by weight of ethyl acrylate.

The copolymers (a) preferably have a molecular weight of more than approximately 100 kDa, preferably approximately 130-160 kDa. The glass transition temperature is preferably between about 80 and about 120° C., in particular between about 85 and about 105° C., more preferably about 90 and about 102° C. The previously described terpolymers as copolymer (a) are sold for example under the name Tilamar® Fix A140 (INCI: Acrylates Copolymer; CAS number: 26715-43-5).

The cosmetic compositions as contemplated herein contain an anionic acrylate copolymer (b) as second essential constituent.

The anionic acrylate copolymer (b) is constructed at least from the following monomer units: at least one (meth)acrylic acid unit (b1), at least one (meth)acrylic acid ethyl ester unit (b2), and at least one (meth)acrylic acid ester unit (b3) which is different from the (meth)acrylic acid ethyl ester unit (b2) and comprises a hydrophobic group as ester group.

The copolymer (b) can be constructed from further monomer units as contemplated herein. In accordance with a preferred embodiment as contemplated herein the copolymer (b), however, is only constructed from the units (b1), (b2) and (b3), i.e. it consists of units derived from these monomer units.

The at least one (meth)acrylic acid unit (b1) can be a methacrylic acid unit or acrylic acid unit, wherein a methacrylic acid unit is preferred.

The at least one (meth)acrylic acid ethyl ester unit (b2) can be a methacrylic acid ethyl ester unit or an acrylic acid ethyl ester unit, wherein an acrylic acid ethyl ester unit is preferred.

The at least one (meth)acrylic acid ester unit (b3) can be a (meth)acrylic acid alkyl ester unit as contemplated herein. The alkyl group of the (meth)acrylic acid alkyl ester unit serves to control the hydrophobicity of the copolymer. The alkyl group is preferably a linear or branched alkyl group with 2 to 30 carbon atoms, more preferably 3 to 12 carbon atoms. As contemplated herein, the hydrophobic group can also be a hydrophobic group other than an alkyl group, for example an aromatic hydrocarbon ester group. A substituted or unsubstituted phenyl ester group or substituted or unsubstituted alkylene phenyl ester group can be cited as examples, for example a benzyl ester group.

The viscosity of the anionic acrylate copolymer (b) used in the cosmetic composition, with a solids content of 2% by weight and neutralized solution at 25° C., is preferably at most about 60,000 to about 120,000 cPS.

Suitable anionic acrylate copolymers (b) are commercially available under the INCI name Acrylates Copolymer (and) Water. The anionic acrylate copolymer (b) AquaStyle® SH-100 polymer from Ashland, Inc. is most preferred. In the commercially available form, this has a solids content of from about 28 to about 32% by weight and a pH value of from about 2.1 to about 4.0.

The cosmetic composition as contemplated herein contains the acrylate copolymer (a) and acrylate copolymer (b) in amounts usual and suitable for styling agents, which amounts can be adapted to the specific application and formulation.

The composition as contemplated herein can contain the copolymer (a) for example in an amount of from about 0.5 to about 10% by weight, in relation to the total weight of the composition as contemplated herein. Preferred proportions of the copolymer (a) are from about 2.0 to about 9.0% by weight, and in particular from about 4.0 to about 8.0% by weight, specified in each case as solids content of active substance in the cosmetic composition.

The cosmetic composition as contemplated herein contains the acrylate copolymer (b), in relation to the total weight of the cosmetic composition, for example in an amount of from about 0.1 to about 5.0% by weight, preferably from about 1.0 to about 4.0% by weight, more preferably from about 1.5 to about 3.0% by weight, specified in each case as solids content of active substance in the cosmetic composition.

Compared to alternative cosmetic products, the cosmetic compositions as contemplated herein are exemplified by an improved long-term hold, in addition to the above-mentioned advantages. A ratio by weight of the polymers a) and b) in the cosmetic product of from about 5:1 to about 1:5, preferably 3:1 to 1:3, and in particular from about 2:1 to about 1:2 has proven to be particularly advantageous for the cosmetic properties of the product as contemplated herein.

In a particularly preferred embodiment as contemplated herein, the cosmetic composition contains, as the anionic acrylate copolymer (a), the copolymer commercially available under the name Tilamar® Fix, and, as the anionic acrylate copolymer (b), the copolymer commercially available under the name AquaStyle™ SH-100. In the case of this combination, particularly good results in terms of a combination of stiffness and long-term hold were attained. This polymer combination is particularly advantageous in the case of styling products in gel form.

Further generally required properties of styling products, such as resistance to moisture and low tack, are attained equally in particular with this combination, particularly when the product is formulated as a hair gel.

The acrylate copolymers (a) and (b) are preferably used in partially neutralized or neutralized form in the cosmetic composition. An alkanolamine is preferably used for the neutralization. The alkanolamines that can be used as alkalizing agent as contemplated herein are preferably selected from primary amines having a $C_2$-$C_6$ alkyl parent substance carrying at least one hydroxyl group. Particularly preferred alkanolamines are selected from the group formed from 2-aminoethan-1-ol (monoethanolamine), tris(2-hydroxyethyl)-amine (triethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol. Alkanolamines that are very particularly preferred as contemplated herein are selected from the group of 2-aminoethan-1-ol, 2-amino-2-methylpropan-1-ol and 2-amino-2-methyl-propan-1,3-diol. A particularly suitable neutralizing agent here has proven to be 2-amino-2-methylpropanol. Cosmetic products that are preferred as contemplated herein therefore contain 2-amino-2-methylpropanol. 2-amino-2-methylpropanol is used in the products as contemplated herein preferably in a quantity that does not exceed the quantity required for neutralization of the acrylate copolymers (a) and (b). The quantities of 2-amino-2-methylpropanol used in the compositions as contemplated herein is preferably from about 80 to about 100%, particularly preferably from about 90 to about 100% and in particular from about 95 to about 100% of the quantity required for full neutralization of the acrylate copolymers (a) and (b). In a preferred embodiment the proportion by weight of 2-amino-2-methylpropanol in the total weight of the cosmetic product is from about 0.05 to about 7.0% by weight, preferably from about 0.1 to about 5.0% by weight, and in particular from about 0.1 to about 3.0% by weight.

To summarize, a preferred cosmetic composition for temporarily reshaping keratin fibres contains, in relation to its total weight:
(a) from about 0.2 to about 4.0 of at least one acrylate copolymer (a) which is constructed at least from the following monomer units:
(a1) n-butyl methacrylate,
(a2) methacrylic acid,
(a3) ethyl acrylate, and
(b) from about 0.1 to about 5.0 of at least one anionic acrylate copolymer (b) which is constructed at least from the following monomer units:
(b1) at least one methacrylic acid unit
(b2) at least one acrylic acid ethyl ester unit
(b3) at least one methacrylic acid ester unit which is different from the acrylic acid ethyl ester unit (b2) and comprises a hydrophobic group as ester group.

The cosmetic composition as contemplated herein preferably contains one or more further component(s) acting as thickening agent or gel former which is/are different from the acrylate copolymers (a) and (b) and likewise assist the film formation. Examples are cationic, anionic, non-ionic or amphoteric polymers. The proportion by weight of these further components in the total weight of the cosmetic composition can be relatively low on account of the presence of the components (a) and (b) and for example is from about 0.02 to about 3% by weight, preferably from about 0.05 to about 1.5% by weight, and even more preferably from about 0.2 to about 0.8% by weight.

Examples are Acrylamide/Ammonium Acrylate Copolymer, Acrylamides/DMAPA Acrylates/Methoxy PEG Methacrylate Copolymer, Acrylamidopropyltrimonium Chloride/Acrylamide Copolymer, Acrylamidopropyltrimonium Chloride/Acrylates Copolymer, Acrylates/Acetoacetoxyethyl Methacrylate Copolymer, Acrylates/Acrylamide Copolymer, Acrylates/Ammonium Methacrylate Copolymer, Acrylates/t-Butylacrylamide Copolymer, Acrylates/C1-2 Succinates/Hydroxyacrylates Copolymer, Acrylates/Lauryl Acrylate/Stearyl Acrylate/Ethylamine Oxide Methacrylate Copolymer, Acrylates/Octylacrylamide Copolymer, Acrylates/Octylacrylamide/Diphenyl Amodimethicone Copolymer, Acrylates/Stearyl Acrylate/Ethylamine Oxide Methacrylate Copolymer, Acrylates/VA Copolymer, Acrylates/VP Copolymer, Adipic Acid/Diethylenetriamine Copolymer, Adipic Acid/Dimethylaminohydroxypropyl Diethylenetriamine Copolymer, Adipic Acid/Epoxypropyl Diethylenetriamine Copolymer, Adipic Acid/Isophthalic Acid/Neopentyl Glycol/Trimethylolpropane Copolymer, Allyl Stearate/VA Copolymer, Aminoethylacrylate Phosphate/Acrylates Copolymer, Aminoethylpropanediol-Acrylates/Acrylamide Copolymer, Aminoethylpropanediol-AMPD-Acrylates/Diacetoneacrylamide Copolymer, Ammonium VA/Acrylates Copolymer, AMPD-Acrylates/Diacetoneacrylamide Copolymer, AMP-Acrylates/Allyl Methacrylate Copolymer, AMP-Acrylates/C1-18 Alkyl Acrylates/C1-8 Alkyl Acrylamide Copolymer, AMP-Acrylates/Diacetoneacrylamide Copolymer, AMP-Acrylates/Dimethylaminoethylmethacrylate Copolymer, Bacillus/Rice Bran Extract/Soybean Extract Ferment Filtrate, Bis-Butyloxyamodimethicone/PEG-60 Copolymer, Butyl Acrylate/Ethylhexyl Methacrylate Copolymer, Butyl Acrylate/Hydroxypropyl Dimethicone Acrylate Copolymer, Butylated PVP, Butyl Ester of Ethylene/MA Copolymer, Butyl Ester of PVM/MA Copolymer, Calcium/Sodium PVM/MA Copolymer, Corn Starch/Acrylamide Sodium Acrylate Copolymer, Diethylene Glycolamine/Epichlorohydrin/Piperazine Copolymer, Dimethicone Crosspolymer, Diphenyl Amodimethicone, Ethyl Ester of PVM/MA Copolymer, Hydrolysed Wheat Protein/PVP Crosspolymer, Isobutylene/Ethylmaleimide/Hydroxyethylmaleimide Copolymer, Isobutylene/MA Copolymer, Isobutylmethacrylate/Bis-Hydroxypropyl Dimethicone Acrylate Copolymer, Isopropyl Ester of PVM/MA Copolymer, Lauryl Acrylate Crosspolymer, Lauryl Methacrylate/Glycol Dimethacrylate Crosspolymer, MEA-Sulfite, Methacrylic Acid/Sodium Acrylamidomethyl Propane Sulfonate Copolymer, Methacryloyl Ethyl Betaine/Acrylates Copolymer, Octylacrylamide/Acrylates/Butylaminoethyl methacrylate Copolymer, PEG/PPG-25/25 Dimethicone/Acrylates Copolymer, PEG-8/SMDI Copolymer, Polyacrylamide, Polyacrylate-6, Polybeta-Alanine/Glutaric Acid Crosspolymer, Polybutylene Terephthalate, Polyester-1, Polyethylacrylate, Polyethylene Terephthalate, Polymethacryloyl Ethyl Betaine, Polypentaerythrityl Terephthalate, Polyperfluoroperhydrophenanthrene, Polyquaternium-1, Polyquaternium-2, Polyquaternium-4, Polyquaternium-5, Polyquaternium-6, Polyquaternium-7, Polyquaternium-8, Polyquaternium-9, Polyquaternium-10, Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-22, Polyquaternium-24, Polyquaternium-27, Polyquaternium-28, Polyquaternium-29, Polyquaternium-30, Polyquaternium-31, Polyquaternium-32, Polyquaternium-33, Polyquaternium-34, Polyquaternium-35, Polyquaternium-36, Polyquaternium-37, Polyquaternium-39, Polyquaternium-45, Polyquaternium-46, Polyquaternium-47, Polyquaternium-48, Polyquaternium-49, Polyquaternium-50, Polyquaternium-55, Polyquaternium-56, Polysilicone-9, Polyurethane-1, Polyurethane-6, Polyurethane-10, Polyvinyl Acetate, Polyvinyl Butyral, Polyvinylcaprolactam, Polyvinylformamide, Polyvinyl Imidazolinium Acetate, Polyvinyl Methyl Ether, Potassium Butyl Ester of PVM/MA Copolymer, Potassium Ethyl Ester of PVM/MA Copolymer, PPG-70 Polyglyceryl-10 Ether, PPG-12/SMDI Copolymer, PPG-1/SMDI Copolymer, PPG-10 Sorbitol, PVM/MA Copolymer, PVP, PVP/VA/Itaconic Acid Copolymer, PVP/VA/Vinyl Propionate Copolymer, Rhizobian Gum, Rosin Acrylate, Shellac, Sodium Butyl Ester of PVM/MA Copolymer, Sodium Ethyl Ester of PVM/MA Copolymer, Sodium Polyacrylate, Sterculia Urens Gum, Terephthalic Acid/Isophthalic Acid/Sodium Isophthalic Acid Sulfonate/Glycol Copolymer, Trimethylolpropane Triacrylate, Trimethylsiloxysilylcarbamoyl Pullulan, VA/Crotonates Copolymer, VA/Crotonates/Methacryloxybenzophenone-1 Copolymer, VA/Crotonates/Vinyl Neodecanoate Copolymer, VA/Crotonates/Vinyl Propionate Copolymer, VA/DBM Copolymer, VA/Vinyl Butyl Benzoate/Crotonates Copolymer, Vinylamine/Vinyl Alcohol Copolymer, Vinyl Caprolactam/VP/Dimethylaminoethyl Methacrylate Copolymer, VP/Acrylates/Lauryl Methacrylate Copolymer, VP/Dimethylaminoethylmethacrylate Copolymer, VP/DMAPA Acrylates Copolymer, VP/Hexadecene Copolymer, VP/VA Copolymer, VP/Vinyl Caprolactam/DMAPA Acrylates Copolymer, Yeast Palmitate and Styrene/VP Copolymer.

Examples of non-ionic polymers are:

Vinylpyrrolidone/vinyl ester copolymers, as are sold for example under the trade name Luviskol (BASF). Luviskol VA 64 and Luviskol VA 73, each vinylpyrrolidone/vinyl acetate copolymers, are preferred non-ionic polymers.

Cellulose ethers, such as hydroxypropyl cellulose, hydroxyethyl cellulose and methylhydroxypropyl cellullose, as are sold for example under the trade names Culminal and Benecel (AQUALON).

Shellac.

Polyvinylpyrrolidones, as are sold for example under the name Luviskol (BASF).

Siloxanes. These siloxanes can be both water-soluble and water-insoluble. Both volatile and non-volatile siloxanes are suitable, wherein compounds of which the boiling point at normal pressure is above 200° C. are understood to be non-volatile siloxanes. Preferred siloxanes are polydialkylsiloxanes, such as polydimethyl siloxane, polyalkylaryl siloxanes, such as polyphenylmethyl siloxane, ethoxylated polydialkyl siloxanes, and polydialkyl siloxanes which contain amine and/or hydroxy groups.

Glycosidically substituted silicones.

The further component acting as gel former is preferably a homopolyacrylic acid (INCI: Carbomer), which is commercially available under the name Carbopol® in various embodiments. The carbomer is preferably contained in a proportion of from about 0.02 to about 3% by weight, preferably from about 0.05 to about 1.5% by weight, and even more preferably from about 0.2 to about 0.8% by weight, in relation to the total weight of the cosmetic composition.

On account of their cosmetic effect in combination with the copolymers a) and b), film-forming polymers used with preference as contemplated herein are in particular the polyvinylpyrrolidones (INCI name: PVP) and the vinylpyrrolidone/vinyl acetate copolymers (INCI name VP/VA copolymer), wherein the proportion by weight of these polymers is preferably limited to quantities between about 1.0 and about 10% by weight. Particularly preferred cosmetic compositions as contemplated herein are therefore exemplified in that they also contain, in relation to their total weight, between about 1.0 and about 10% by weight of polyvinylpyrrolidone and/or vinylpyrrolidone/vinyl acetate copolymer, preferably polyvinylpyrrolidone. Particularly preferred cosmetic products have a proportion by weight of the polyvinylpyrrolidone and/or vinylpyrrolidone/vinyl acetate copolymer c) in the total weight of the cosmetic preparation of from about 2.0 to about 8.5% by weight, preferably from about 3.0 to about 7.0% by weight.

The cosmetic composition as contemplated herein can contain further conventional substances of styling products. In particular, additional nourishing ingredients can be mentioned as further auxiliaries and additives.

As nourishing ingredient, the product can contain at least one protein hydrolysate and/or a derivative thereof, for example. Protein hydrolysates are product mixtures which are obtained by acid-catalyzed, base-catalyzed or enzymatically catalyzed breakdown of proteins (albumens). The term "protein hydrolysates" is understood as contemplated herein to also mean total hydrolysates and also individual amino acids and derivatives thereof as well as mixtures of different amino acids. The molecular weight of the protein hydrolysates usable as contemplated herein lies between about 75, the molecular weight for glycine, and about 200,000, and the molecular weight is preferably from about 75 to about 50,000, and very particularly preferably from about 75 to about 20,000 daltons.

As nourishing ingredient, the product as contemplated herein can also contain at least one vitamin, a provitamin, a vitamin precursor and/or one of the derivatives thereof. Here, vitamins, provitamins and vitamin precursors that are usually assigned to the groups A, B, C, E, F and H are preferred as contemplated herein.

Similarly to the addition of glycerol and/or propylene glycol, the addition of panthenol increases the flexibility of the polymer film formed with application of the product as contemplated herein.

As nourishing ingredient, the products as contemplated herein can also contain at least one plant extract, but also monosaccharides or oligosaccharides and/or lipids.

Oil bodies are also suitable as nourishing ingredient. Natural and synthetic cosmetic oil bodies include, for example, plant oils, liquid paraffin oils, isoparaffin oils and synthetic hydrocarbons as well as di-n-alkyl ethers having a total of between 12 and 36 C atoms, in particular 12 to 24 C atoms. Preferred cosmetic products as contemplated herein contain at least one oil body, preferably at least one oil body from the group of silicone oils. The group of silicone oils includes, in particular, the dimethicones, which also include the cyclomethicones, the aminofunctional silicones, and also the dimethiconols. The dimethicones can be both linear and branched and cyclic, or cyclic and branched. Suitable silicone oils or silicone gums are in particular dialkyl and alkylaryl siloxanes, such as dimethyl polysiloxane and methylphenyl polysiloxane, and the alkoxylated, quatemised, or anionic derivatives thereof. Cyclic and linear polydialkyl siloxanes, the alkoxylated and/or aminised derivatives thereof, dihydroxypolydimethyl siloxanes and polyphenyl alkyl siloxanes are preferred.

Ester oils, i.e. esters of C6-C30 fatty acids with C2-C30 fatty alcohols, preferably monoesters of the fatty acids with alcohols having 2 to 24 C atoms, such as isopropylmyristate (Rilanit® IPM), isononanoic acid C16-18 alkyl ester (Cetiol® SN), 2-ethylhexyl palmitate (Cegesoft® 24), stearic acid-2-ethylhexyl ester (Cetiol® 868), cetyl oleate, glycerol tricaprylate, coconut fatty alcohol caprate/caprylate (Cetiol® LC), n-butyl stearate, oleyl erucate (Cetiol® J 600), isopropyl palmitate (Rilanite® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), and oleic acid decyl ester (Cetiol® V) are further preferred nourishing oil bodies.

Furthermore, dicarboxylic acid esters, symmetrical, asymmetrical or cyclic esters of carbon dioxide with fatty alcohols, tri fatty acid esters of saturated and/or unsaturated linear and/or branched fatty acids with glycerol or fatty acid partial glycerides, which are understood to mean monoglycerides, diglycerides and industrial mixtures thereof, are to be understood as nourishing ingredients.

Emulsifiers or surface-active agents are also preferably contained in the composition as contemplated herein. PEG derivatives of hydrogenated castor oil which are obtainable for example under the name PEG Hydrogenated Castor Oil are preferred, for example PEG-30 Hydrogenated Castor Oil, PEG-33 Hydrogenated Castor Oil, PEG-35 Hydrogenated Castor Oil, PEG-36 Hydrogenated Castor Oil, or PEG-40 Hydrogenated Castor Oil. The use of PEG-40 Hydrogenated Castor Oil is preferred as contemplated herein. These are preferably contained in an amount of from about 0.05 to about 1.5% by weight, more preferably from about 0.1 to about 1.0% by weight, also preferably from about 0.2 to about 0.8% by weight or from about 0.3 to about 0.6% by weight.

The cosmetic products as contemplated herein contain the ingredients or active substances in a cosmetically acceptable carrier.

Preferred cosmetically acceptable carriers are aqueous, alcoholic, or aqueous-alcoholic media with preferably at least 10% by weight water, calculated on the basis of the total weight of the product.

The cosmetic carrier particularly preferably contains water, in particular in such an amount that the cosmetic product, calculated on the basis of the total weight of the product, contains at least about 10% by weight, in particular at least about 20.0% by weight, most preferably at least 40% by weight. Cosmetic products that are very particularly preferred comprise, in relation to their total weight, a water content between about 50 and about 95% by weight, preferably between about 60 and about 90% by weight, and in particular between about 65 and about 85% by weight.

As alcohols, the lower alcohols with 1 to 4 carbon atoms usually used in particular for cosmetic purposes, such as ethanol and isopropanol, can be contained.

Examples of water-soluble solvents as cosolvents are glycerol and/or ethylene glycol and/or 1,2-propylene glycol in an amount of from about 0 to about 30% by weight in relation to the total product.

Table Overview

The composition of some preferred cosmetic products can be deduced from the following tables (specified amounts in % by weight in relation to the total weight of the cosmetic product unless specified otherwise).

|  | Formula 1 | Formula 2 | Formula 3 | Formula 4 | Formula 5 |
| --- | --- | --- | --- | --- | --- |
| Copolymer (a) | 0.2 to 4.0 | 1.0 to 3.5 | 1.0 to 3.5 | 1.5 to 3.0 | 1.5 to 3.0 |
| Copolymer (b) | 0.1 to 5.0 | 0.1 to 5.0 | 1.0 to 4.0 | 1.0 to 4.0 | 1.5 to 3.0 |
| Misc | to 100 | to 100 | to 100 | to 100 | to 100 |

|  | Formula 1a | Formula 2a | Formula 3a | Formula 4a | Formula 5a |
| --- | --- | --- | --- | --- | --- |
| Copolymer a): Acrylates Copolymer | 0.2 to 4.0 | 1.0 to 3.5 | 1.0 to 3.5 | 1.5 to 3.0 | 1.5 to 3.0 |
| Copolymer (b): Acrylates Copolymer (and) Water | 0.1 to 5.0 | 0.1 to 5.0 | 1.0 to 4.0 | 1.0 to 4.0 | 1.5 to 3.0 |
| Misc | to 100 | to 100 | to 100 | to 100 | to 100 |

|  | Formula 1b | Formula 2b | Formula 3b | Formula 4b | Formula 5b |
| --- | --- | --- | --- | --- | --- |
| Copolymer a): Tilamar ® Fix A140 (specified as solids content) | 0.2 to 4.0 | 1.0 to 3.5 | 1.0 to 3.5 | 1.5 to 3.0 | 1.5 to 3.0 |
| Copolymer (b): AquaStyle ® SH-100 (specified as solids content) | 0.1 to 5.0 | 0.1 to 5.0 | 1.0 to 4.0 | 1.0 to 4.0 | 1.5 to 3.0 |
| Misc | to 100 | to 100 | to 100 | to 100 | to 100 |

|  | Formula 6 | Formula 7 | Formula 8 | Formula 9 | Formula 10 |
| --- | --- | --- | --- | --- | --- |
| Copolymer (a) | 0.2 to 4.0 | 1.0 to 3.5 | 1.0 to 3.5 | 1.5 to 3.0 | 1.5 to 3.0 |
| Copolymer (b) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

|  | Formula 6a | Formula 7a | Formula 8a | Formula 9a | Formula 10a |
| --- | --- | --- | --- | --- | --- |
| Copolymer a): Acrylates Copolymer | 0.2 to 4.0 | 1.0 to 3.5 | 1.0 to 3.5 | 1.5 to 3.0 | 1.5 to 3.0 |
| Copolymer (b): Acrylates Copolymer (and) Water | 0.1 to 5.0 | 0.1 to 5.0 | 1.0 to 4.0 | 1.0 to 4.0 | 1.5 to 3.0 |

-continued

| | | | | | |
|---|---|---|---|---|---|
| Polyvinyl-pyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

| | Formula 6b | Formula 7b | Formula 8b | Formula 9b | Formula 10b |
|---|---|---|---|---|---|
| Copolymer a): Tilamar ® Fix A140 (specified as solids content) | 0.2 to 4.0 | 1.0 to 3.5 | 1.0 to 3.5 | 1.5 to 3.0 | 1.5 to 3.0 |
| Copolymer (b): AquaStyle ® SH-100 (specified as solids content) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

| | Formula 11 | Formula 12 | Formula 13 | Formula 14 | Formula 15 |
|---|---|---|---|---|---|
| Copolymer (a) | 0.2 to 4.0 | 1.0 to 3.5 | 1.0 to 3.5 | 1.5 to 3.0 | 1.5 to 3.0 |
| Copolymer (b) | 0.1 to 5.0 | 0.1 to 5.0 | 1.0 to 4.0 | 1.0 to 4.0 | 1.5 to 3.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

| | Formula 11a | Formula 12a | Formula 13a | Formula 14a | Formula 15a |
|---|---|---|---|---|---|
| Copolymer a): Acrylates Copolymer | 0.2 to 4.0 | 1.0 to 3.5 | 1.0 to 3.5 | 1.5 to 3.0 | 1.5 to 3.0 |
| Copolymer (b): Acrylates Copolymer (and) Water | 0.1 to 5.0 | 0.1 to 5.0 | 1.0 to 4.0 | 1.0 to 4.0 | 1.5 to 3.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

| | Formula 11b | Formula 12b | Formula 13b | Formula 14b | Formula 15b |
|---|---|---|---|---|---|
| Copolymer a): Tilamar ® Fix A140 (specified as solids content) | 0.2 to 4.0 | 1.0 to 3.5 | 1.0 to 3.5 | 1.5 to 3.0 | 1.5 to 3.0 |
| Copolymer (b): AquaStyle ® SH-100 (specified as solids content) | 0.1 to 5.0 | 0.1 to 5.0 | 1.0 to 4.0 | 1.0 to 4.0 | 1.5 to 3.0 |
| Vinylpyrrolidone/vinyl acetate copolymer | 1.0 to 10 | 2.0 to 8.5 | 2.0 to 8.5 | 3.0 to 7.0 | 3.0 to 7.0 |
| Misc | to 100 | to 100 | to 100 | to 100 | to 100 |

| | Formula 16 | Formula 17 | Formula 18 | Formula 19 | Formula 20 |
|---|---|---|---|---|---|
| Copolymer (a) | 0.2 to 4.0 | 1.0 to 3.5 | 1.0 to 3.5 | 1.5 to 3.0 | 1.5 to 3.0 |
| Copolymer (b) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | to 100 | to 100 | to 100 | to 100 | to 100 |

| | Formula 16a | Formula 17a | Formula 18a | Formula 19a | Formula 20a |
|---|---|---|---|---|---|
| Copolymer a): Acrylates Copolymer | 0.2 to 4.0 | 1.0 to 3.5 | 1.0 to 3.5 | 1.5 to 3.0 | 1.5 to 3.0 |
| Copolymer (b): Acrylates Copolymer (and) Water | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | to 100 | to 100 | to 100 | to 100 | to 100 |

-continued

|  | Formula 16b | Formula 17b | Formula 18b | Formula 19b | Formula 20b |
| --- | --- | --- | --- | --- | --- |
| Copolymer a): Tilamar ® Fix A140 (specified as solids content) | 0.2 to 4.0 | 1.0 to 3.5 | 1.0 to 3.5 | 1.5 to 3.0 | 1.5 to 3.0 |
| Copolymer (b): AquaStyle ® SH-100 (specified as solids content) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Misc | to 100 | to 100 | to 100 | to 100 | to 100 |

|  | Formula 21 | Formula 22 | Formula 23 | Formula 24 | Formula 25 |
| --- | --- | --- | --- | --- | --- |
| Copolymer (a) | 0.2 to 4.0 | 1.0 to 3.5 | 1.0 to 3.5 | 1.5 to 3.0 | 1.5 to 3.0 |
| Copolymer (b) | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | to 100 | to 100 | to 100 | to 100 | to 100 |

|  | Formula 21a | Formula 22a | Formula 23a | Formula 24a | Formula 25a |
| --- | --- | --- | --- | --- | --- |
| Copolymer a): Acrylates Copolymer | 0.2 to 4.0 | 1.0 to 3.5 | 1.0 to 3.5 | 1.5 to 3.0 | 1.5 to 3.0 |
| Copolymer (b): Acrylates Copolymer (and) Water | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | to 100 | to 100 | to 100 | to 100 | to 100 |

|  | Formula 21b | Formula 22b | Formula 23b | Formula 24b | Formula 25b |
| --- | --- | --- | --- | --- | --- |
| Copolymer a): Tilamar ® Fix A140 (specified as solids content) | 0.2 to 4.0 | 1.0 to 3.5 | 1.0 to 3.5 | 1.5 to 3.0 | 1.5 to 3.0 |
| Copolymer (b): AquaStyle ® SH-100 (specified as solids content) | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Misc | to 100 | to 100 | to 100 | to 100 | to 100 |

|  | Formula 26 | Formula 27 | Formula 28 | Formula 29 | Formula 30 |
| --- | --- | --- | --- | --- | --- |
| Copolymer (a) | 0.2 to 4.0 | 1.0 to 3.5 | 1.0 to 3.5 | 1.5 to 3.0 | 1.5 to 3.0 |
| Copolymer (b) | 0.1 to 5.0 | 0.1 to 5.0 | 1.0 to 4.0 | 1.0 to 4.0 | 1.5 to 3.0 |
| Water | 50 to 95 | 50 to 95 | 60 to 90 | 60 to 90 | 65 to 85 |
| Misc | to 100 | to 100 | to 100 | to 100 | to 100 |

|  | Formula 26a | Formula 27a | Formula 28a | Formula 29a | Formula 30a |
| --- | --- | --- | --- | --- | --- |
| Copolymer a): Acrylates Copolymer | 0.2 to 4.0 | 1.0 to 3.5 | 1.0 to 3.5 | 1.5 to 3.0 | 1.5 to 3.0 |
| Copolymer (b): Acrylates Copolymer (and) Water | 0.1 to 5.0 | 0.1 to 5.0 | 1.0 to 4.0 | 1.0 to 4.0 | 1.5 to 3.0 |
| Water | 50 to 95 | 50 to 95 | 60 to 90 | 60 to 90 | 65 to 85 |
| Misc | to 100 | to 100 | to 100 | to 100 | to 100 |

|  | Formula 26b | Formula 27b | Formula 28b | Formula 29b | Formula 30b |
|---|---|---|---|---|---|
| Copolymer a): Tilamar ® Fix A140 (specified as solids content) | 0.2 to 4.0 | 1.0 to 3.5 | 1.0 to 3.5 | 1.5 to 3.0 | 1.5 to 3.0 |
| Copolymer (b): AquaStyle ® SH-100 (specified as solids content) | 0.1 to 5.0 | 0.1 to 5.0 | 1.0 to 4.0 | 1.0 to 4.0 | 1.5 to 3.0 |
| Water Misc | 50 to 95 to 100 | 50 to 95 to 100 | 60 to 90 to 100 | 60 to 90 to 100 | 65 to 85 to 100 |

|  | Formula 31 | Formula 32 | Formula 33 | Formula 34 | Formula 35 |
|---|---|---|---|---|---|
| Copolymer (a) | 0.2 to 4.0 | 1.0 to 3.5 | 1.0 to 3.5 | 1.5 to 3.0 | 1.5 to 3.0 |
| Copolymer (b) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Water Misc | 50 to 95 to 100 | 50 to 95 to 100 | 60 to 90 to 100 | 60 to 90 to 100 | 65 to 85 to 100 |

|  | Formula 31a | Formula 32a | Formula 33a | Formula 34a | Formula 35a |
|---|---|---|---|---|---|
| Copolymer a): Acrylates Copolymer | 0.2 to 4.0 | 1.0 to 3.5 | 1.0 to 3.5 | 1.5 to 3.0 | 1.5 to 3.0 |
| Copolymer (b): Acrylates Copolymer (and) Water | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Water Misc | 50 to 95 to 100 | 50 to 95 to 100 | 60 to 90 to 100 | 60 to 90 to 100 | 65 to 85 to 100 |

|  | Formula 31b | Formula 32b | Formula 33b | Formula 34b | Formula 35b |
|---|---|---|---|---|---|
| Copolymer a): Tilamar ® Fix A140 (specified as solids content) | 0.2 to 4.0 | 1.0 to 3.5 | 1.0 to 3.5 | 1.5 to 3.0 | 1.5 to 3.0 |
| Copolymer (b): AquaStyle ® SH-100 (specified as solids content) | 0.1 to 5.0 | 0.1 to 5.0 | 1.0 to 4.0 | 1.0 to 4.0 | 1.5 to 3.0 |
| Polyvinyl-pyrrolidone | 1.0 to 10 | 2.0 to 8.5 | 2.0 to 8.5 | 3.0 to 7.0 | 3.0 to 7.0 |
| Water Misc | 50 to 95 to 100 | 50 to 95 to 100 | 60 to 90 to 100 | 60 to 90 to 100 | 65 to 85 to 100 |

|  | Formula 36 | Formula 37 | Formula 38 | Formula 39 | Formula 40 |
|---|---|---|---|---|---|
| Copolymer (a) | 0.2 to 4.0 | 1.0 to 3.5 | 1.0 to 3.5 | 1.5 to 3.0 | 1.5 to 3.0 |
| Copolymer (b) | 0.1 to 5.0 | 0.1 to 5.0 | 1.0 to 4.0 | 1.0 to 4.0 | 1.5 to 3.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Water Misc | 50 to 95 to 100 | 50 to 95 to 100 | 60 to 90 to 100 | 60 to 90 to 100 | 65 to 85 to 100 |

|  | Formula 36a | Formula 37a | Formula 38a | Formula 39a | Formula 40a |
|---|---|---|---|---|---|
| Copolymer a): Acrylates Copolymer | 0.2 to 4.0 | 1.0 to 3.5 | 1.0 to 3.5 | 1.5 to 3.0 | 1.5 to 3.0 |
| Copolymer (b): Acrylates Copolymer (and) Water | 0.1 to 5.0 | 0.1 to 5.0 | 1.0 to 4.0 | 1.0 to 4.0 | 1.5 to 3.0 |

-continued

|  | | | | | |
|---|---|---|---|---|---|
| Vinylpyrrolidone/ vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 36b | Formula 37b | Formula 38b | Formula 39b | Formula 40b |
|---|---|---|---|---|---|
| Copolymer a): Tilamar ® Fix A140 (specified as solids content) | 0.2 to 4.0 | 1.0 to 3.5 | 1.0 to 3.5 | 1.5 to 3.0 | 1.5 to 3.0 |
| Copolymer (b): AquaStyle ® SH-100 (specified as solids content) | 0.1 to 5.0 | 0.1 to 5.0 | 1.0 to 4.0 | 1.0 to 4.0 | 1.5 to 3.0 |
| Vinylpyrrolidone/ vinyl acetate copolymer | 1.0 to 10 | 2.0 to 8.5 | 2.0 to 8.5 | 3.0 to 7.0 | 3.0 to 7.0 |
| Water | 50 to 95 | 50 to 95 | 60 to 90 | 60 to 90 | 65 to 85 |
| Misc | to 100 | to 100 | to 100 | to 100 | to 100 |

|  | Formula 41 | Formula 42 | Formula 43 | Formula 44 | Formula 45 |
|---|---|---|---|---|---|
| Copolymer (a) | 0.2 to 4.0 | 1.0 to 3.5 | 1.0 to 3.5 | 1.5 to 3.0 | 1.5 to 3.0 |
| Copolymer (b) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | to 100 | to 100 | to 100 | to 100 | to 100 |

|  | Formula 41a | Formula 42a | Formula 43a | Formula 44a | Formula 45a |
|---|---|---|---|---|---|
| Copolymer a): Acrylates Copolymer | 0.2 to 4.0 | 1.0 to 3.5 | 1.0 to 3.5 | 1.5 to 3.0 | 1.5 to 3.0 |
| Copolymer (b): Acrylates Copolymer (and) Water | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | to 100 | to 100 | to 100 | to 100 | to 100 |

|  | Formula 41b | Formula 42b | Formula 43b | Formula 44b | Formula 45b |
|---|---|---|---|---|---|
| Copolymer a): Tilamar ® Fix A140 (specified as solids content) | 0.2 to 4.0 | 1.0 to 3.5 | 1.0 to 3.5 | 1.5 to 3.0 | 1.5 to 3.0 |
| Copolymer (b): AquaStyle ® SH-100 (specified as solids content) | 0.1 to 5.0 | 0.1 to 5.0 | 1.0 to 4.0 | 1.0 to 4.0 | 1.5 to 3.0 |
| Carbomer | 0.02 to 3.0 | 0.05 to 2.0 | 0.05 to 1.5 | 0.2 to 1.0 | 0.4 to 0.8 |
| Water | 50 to 95 | 50 to 95 | 60 to 90 | 60 to 90 | 65 to 85 |
| Misc | to 100 | to 100 | to 100 | to 100 | to 100 |

|  | Formula 46 | Formula 47 | Formula 48 | Formula 49 | Formula 50 |
|---|---|---|---|---|---|
| Copolymer (a) | 0.2 to 4.0 | 1.0 to 3.5 | 1.0 to 3.5 | 1.5 to 3.0 | 1.5 to 3.0 |
| Copolymer (b) | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | to 100 | to 100 | to 100 | to 100 | to 100 |

|  | Formula 46a | Formula 47a | Formula 48a | Formula 49a | Formula 50a |
|---|---|---|---|---|---|
| Copolymer a): Acrylates Copolymer | 0.2 to 4.0 | 1.0 to 3.5 | 1.0 to 3.5 | 1.5 to 3.0 | 1.5 to 3.0 |

-continued

| | Formula 41b | Formula 42b | Formula 43b | Formula 44b | Formula 45b |
|---|---|---|---|---|---|
| Copolymer (b): Acrylates Copolymer (and) Water | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | to 100 | to 100 | to 100 | to 100 | to 100 |

| | Formula 46b | Formula 47b | Formula 48b | Formula 49b | Formula 50b |
|---|---|---|---|---|---|
| Copolymer a): Tilamar ® Fix A140 (specified as solids content) | 0.2 to 4.0 | 1.0 to 3.5 | 1.0 to 3.5 | 1.5 to 3.0 | 1.5 to 3.0 |
| Copolymer (b): AquaStyle ® SH-100 (specified as solids content) | 0.1 to 5.0 | 0.1 to 5.0 | 1.0 to 4.0 | 1.0 to 4.0 | 1.5 to 3.0 |
| PEG-40 Hydrogenated Castor Oil | 0.05 to 1.5 | 0.1 to 1.0 | 0.2 to 0.9 | 0.3 to 0.8 | 0.4 to 0.6 |
| Water | 50 to 95 | 50 to 95 | 60 to 90 | 60 to 90 | 65 to 85 |
| Misc | to 100 | to 100 | to 100 | to 100 | to 100 |

The entry "Misc" is to be understood as contemplated herein to mean a cosmetic carrier, in particular water (unless listed separately) and optionally further usual constituents of styling products.

The cosmetic composition as contemplated herein can be formulated in the forms that are usual for the temporary reshaping of hair, for example as a hair gel, hairspray, hair mousse, or hair wax. The cosmetic composition is preferably formulated as a hair gel.

Both hair mousses and hairsprays require the presence of propellants. As contemplated herein, however, no hydrocarbons or only small quantities of hydrocarbons should preferably be used for this. Propane, propane/butane mixtures and dimethyl ethers are particularly suitable propellants as contemplated herein.

The present disclosure also relates to the use of cosmetic compositions as contemplated herein for temporarily reshaping keratin fibres, in particular human hair, and to a method for the temporary shaping of keratin fibres, in particular human hair, in which the cosmetic composition as contemplated herein is applied to keratin fibres.

A further subject of this patent application is the use of a cosmetic composition as contemplated herein to improve the moisture resistance of temporarily shaped keratin fibres.

EXAMPLES

1. The following hair gel was prepared:

| Component/raw material | INCI name or chemical name | V1 | V2 | E1 |
|---|---|---|---|---|
| Tilamar ® Fix A140[1] | Acrylates Copolymer | 12.5 | — | 6.25 |
| AquaStyle SH-100[2] | Acrylates Copolymer (and) Water | — | 16.5 | 8.25 |
| AMP-ULTRA PC 2000 | Aminomethyl propanol | 3.0 | 0.3 | 0.3 |
| Water | | 84.5 | 83.2 | 85.2 |
| Total | | 100 | 100 | 100 |

[1] 40% by weight active substance in water
[2] 30% by weight active substance in water The amounts specified in the table are given in % by weight of the respective raw materials, in relation to the total composition. The polymer content in each of the compositions V1, V2 and E1 was 5.0% by weight.

The moisture resistance of cleaned strands of hair (Kerling) was determined for the obtained styling products by employing an HHCR test (high humidity curl retention test: 6 h; mean value from 5 hair strands in each case):

| | V1 | V2 | E1 |
|---|---|---|---|
| HHCR | 67% | 72% | 86% |

The polymer combination E1 as contemplated herein therefore demonstrated a synergistic effect, going considerably beyond a purely additive effect, in respect of the moisture resistance.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodi-

The invention claimed is:

1. A cosmetic composition for temporarily reshaping keratin fibres, said composition consisting of:
    an acrylate copolymer (a) which is constructed exclusively from the following monomer units;
        from about 60 to about 80% by weight of n-butyl methacrylate,
        from about 10 to about 30% by weight of methacrylic acid, and
        from about 5 to about 15% by weight of ethyl acrylate;
    an anionic acrylate copolymer (b) which is constructed exclusively from the following monomer units;
        methacrylic acid,
        ethyl acrylate, and
        at least one (meth)acrylic acid alkyl ester;
    at least one alkanolamine; and
    water in a proportion of from about 50 to about 95% by weight in relation to the total weight of the cosmetic composition.

2. The cosmetic composition according to claim 1, wherein the composition comprises the copolymer (a) in a proportion of from about 1.5 to about 3.0% by weight in relation to the total weight of the cosmetic composition.

3. The cosmetic composition according to claim 2, wherein the composition comprises the anionic acrylate copolymer (b) in a proportion of from about 0.1 to about 5.0% by weight in relation to the total weight of the cosmetic composition.

4. The cosmetic composition according to claim 1, wherein the composition is present in the form of a hair gel, hair mousse or hair wax.

5. The cosmetic composition according to claim 1, wherein the cosmetic composition is utilized for temporarily reshaping keratin fibres.

6. A method for the temporary shaping of keratin fibres, the method comprising applying the cosmetic composition according to claim 1 to keratin fibres.

7. The cosmetic composition according to claim 1, wherein the copolymer (a) is produced by emulsion polymerization.

8. The cosmetic composition according to claim 1, wherein the anionic acrylate copolymer (b), with a solids content of 2% by weight in an aqueous neutralized solution at 25° C., has a viscosity of from about 60,000 to about 120,000 cPs.

9. The cosmetic composition according to claim 1, wherein the at least one alkanolamine comprises 2-aminoethan-1-ol, 2-amino-2-methylpropan-1-ol, 2-amino-2-methyl-propan-1,3-diol, or combinations thereof.

* * * * *